United States Patent [19]

Hardtmann et al.

[11] Patent Number: 4,760,065
[45] Date of Patent: Jul. 26, 1988

[54] TRIFLUOROMETHYL SUBSTITUTED TETRACYCLIC QUINAZOLIN-ONES HAVING TRANQUILIZING ACTIVITY

[76] Inventors: Goetz E. Hardtmann, 12 Lynnfield Dr., Morristown, N.J. 07960; William J. Houlihan, 15 Raynold Rd., Mt. Lakes, N.J. 07046; Rudolf K. A. Giger, Baselstrasse 22B, CH-4125 Riehen, Switzerland

[21] Appl. No.: 829,594

[22] Filed: Feb. 13, 1986

[51] Int. Cl.$^4$ ............... A61K 31/505; C07D 471/14
[52] U.S. Cl. ................... 514/257; 544/247; 544/282; 546/121; 546/245; 546/246
[58] Field of Search ............ 544/247; 514/257

[56] References Cited

U.S. PATENT DOCUMENTS

| | | | |
|---|---|---|---|
| 3,280,117 | 10/1966 | Griot | 544/250 X |
| 3,598,823 | 8/1971 | Hardtmann | 544/250 |
| 3,621,025 | 11/1971 | Jen et al. | 544/250 |
| 3,631,046 | 12/1971 | Hardtmann | 544/247 |
| 3,963,720 | 6/1976 | Hardtmann | 544/247 |
| 4,000,275 | 12/1976 | Lunn | 514/257 |
| 4,451,448 | 5/1984 | Hardtmann et al. | 544/250 X |
| 4,451,464 | 5/1984 | Hardtmann et al. | 424/251 |
| 4,452,787 | 6/1984 | Hardtmann et al. | 544/250 X |

OTHER PUBLICATIONS

Kabbe, Justus Liebigs Ann Chem, 1978, (3), pp. 398–404 (1978).

Primary Examiner—Donald G. Daus
Assistant Examiner—Diana G. Rivers
Attorney, Agent, or Firm—Gerald D. Sharkin; Richard E. Vila

[57] ABSTRACT

Trifluoromethyl substituted tetracyclic compounds including optical isomers thereof having the formula:

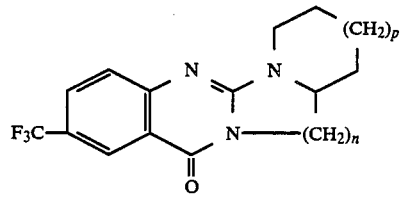

wherein n is 1 or 2 and p is 0 or 1, are useful as CNS agents with tranquilizing effects.

5 Claims, No Drawings

TRIFLUOROMETHYL SUBSTITUTED TETRACYCLIC QUINAZOLIN-ONES HAVING TRANQUILIZING ACTIVITY

The present invention relates to fused ring tetracyclic compounds which are substituted by a trifluoromethyl group, and to methods and compositions for utilizing the same as pharmacological agents, more particularly as minor tranquilizers (anti-anxiety agents) with reduced sedative effects.

The compounds of the present invention are represented by the following structural formula:

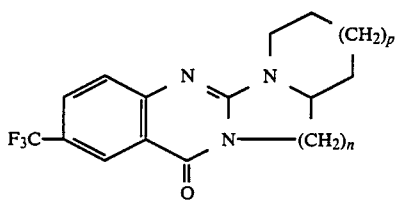

wherein
n is 1 or 2, and
p is 0 or 1,
and the invention includes the optical isomers thereof.

The compounds of the formula I in racemate form may be conveniently prepared by procedures similar or analogous to those described in U.S. Pat. No. 3,631,046.

Thus, a preferred method of preparation of compounds of formula I in which n is 1 involves reacting in a Step A anthranilic acid of formula II:

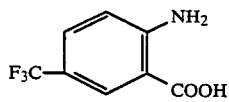

with a compound of formula III:

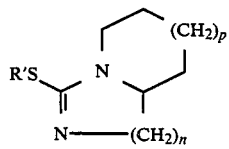

wherein R' is lower alkyl or benzyl, and n and p are as above defined, to obtain a compound of the formula I:

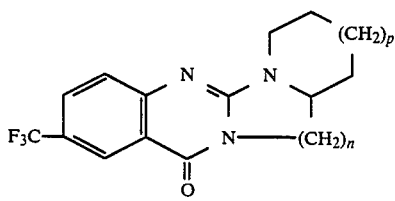

wherein n and p are as defined.

The preparation of compounds I by the reaction of Step A may be suitably carried out at elevated temperatures typically in the range of from 100° C. to 200° C., preferably 140° C. to 180° C. The reaction is conveniently carried out in an inert organic solvent of conventional type, preferably a high boiling organic solvent such as dimethylacetamide and dimethylformamide, more preferably dimethylacetamide. The reaction products of formula I may be recovered from the reaction mixtures of Step A by working up by established procedures.

An alternate process for the preparation of compounds of formula IA (compounds of the formula I in which n is 1) involves the reaction in a Step B of the isatoic anhydride of formula IV:

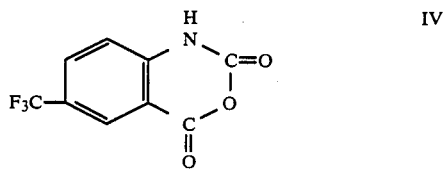

with a compound of formula III in which n is 1, whereby compounds of formula IA are obtained.

The preparation of compounds IA by the reaction of Step B may be carried out at elevated temperatures in the range of 60° C. to 140° C., preferably 80° C. to 120° C. The reaction is conveniently carried in an organic solvent of conventional type providing an inert reaction medium. Cyclic ethers suitable for use at reflux temperatures represent preferred solvents, particularly dioxane. In general, the reaction product of formula IA may be recovered from the reaction of Step B by working up by conventional procedures.

The compounds of formulae II, III and IV employed as starting material in Steps A and B are either known or can be prepared from known materials by procedures analogous to those for preparing the known compounds, for example, where applicable, as described in the above referred to U.S. Pat. No. 3,631,046 when the compounds III in which p is 1 are described. See also J. H. Gogerty et al., Tetracyclic Quinazolinone Derivatives, J. Med. Chem., 14, 878 (1971). The compounds III in which p is 0 may be prepared respectively from 2-aminomethylpyrrolidine (Chem. Abstracts 63, 6840h; 1965) and 2-aminoethylpyrrolidine (Chem. Ber., 92, 637; 1959) by reaction with carbon disulfide analogously to the procedure described in U.S. Pat. No. 3,631,046.

Alternate routes to preparation of the compounds of the formula I and their individual D and L isomers have also been found.

In accord with a procedure for both racemic mixtures and individual isomers the iodo derivatives of the formula V:

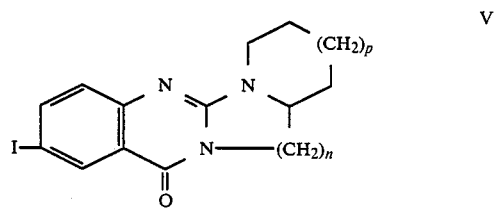

wherein n is 1 or 2 and p 0 or 1, is reacted (Step C) with trifluoroacetic acid or salt thereof and cuprous iodide in the presence of N-methylpyrrolidone. The reaction may be carried out at temperatures of from 80° C. to 200° C., preferably 120° C. to 180° C., and desirably in an inert atmosphere, eg. argon. The product of the formula I may be isolated and recovered by working up of the reaction mixture by conventional procedures.

The compounds of the formula V may be prepared by reaction (Step D) a compound of the formula VI:

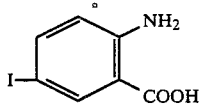
VI with a compound of the formula IIIC:

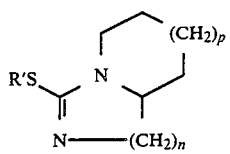
IIIC wherein R', n and p are as above defined, said compound of the formula IIIC being in racemic mixture form or in the form of substantially either the D or L isomer, depending upon the desired product. The reaction may be carried out similarly to the reaction of Steps A and B, described above.

The compounds of the formula VI are either known or may be prepared by known procedures analogously to the known compounds, see Beilstein 14, 373.

The compounds of the formula III in which n is 1 and p is 0 in the form of their individual R- or S-optical isomers may be prepared as represented by the following reaction scheme in which n is as above defined.

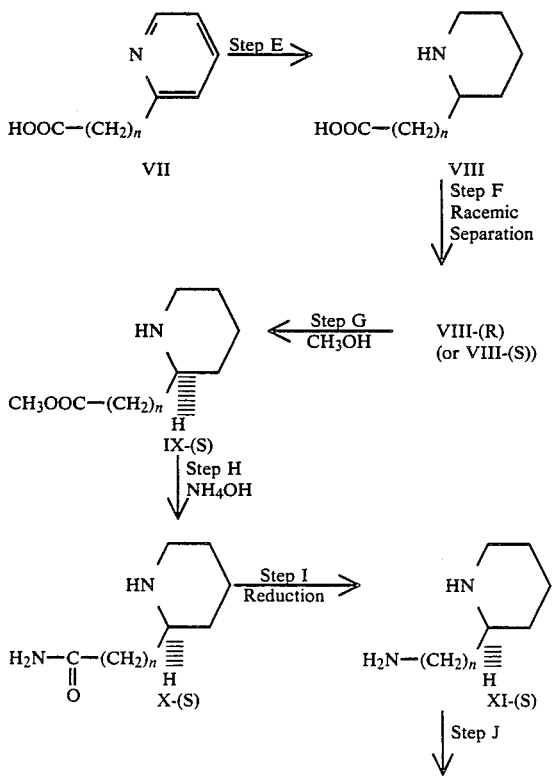

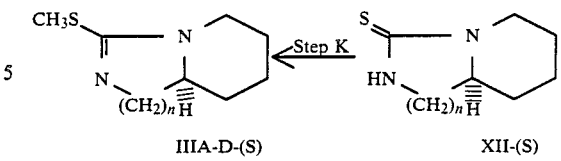

The S isomer (IIIA-(S)) may be prepared by selecting the S-) isomer of the formula VIII(S)- from Step F in the above reaction scheme and then continuing with Steps G through K.

Step E may be effected using hydrogen gas in the presence of a hydrogenation catalyst such as platinum oxide in a suitable solvent, eg. acetic acid, under pressure, preferably 300 to 800 psi and at moderate temperatures, preferably 30°-70° C. The reaction product of the formula VIII is a racemic mixture which may be isolated and recovered by conventional procedures.

In Step F the optical isomers are resolved using, for example, standard individual isomeric forms such as L-(+)-tartaric acid and D-(−)-tartaric acid which will form an acid addition salt with the compound of the formula VIII. A particular form of the standard, eg. L-(+)-tartaric acid, to form the (+)(+) isomeric salt and the (+)(−) isomeric form which may then be readily separated by crystallization to obtain one of the forms. The salt form obtained on crystallization may be treated to liberate the tartaric acid by conventional procedures such as in an appropriate ion exchange column to obtain the desired individual optional isomer of the formula VIII(S) or VIII(R). The form not obtained by the crystallization may be obtained by using a different crystallization procedure or repeating the procedure with the other tartaric acid form, but is usually more conveniently obtained by working up the mother liquor from the crystallization which yielded the first obtained form.

Step G (working with VIII(S) optical form) may be carried out in a conventional manner for forming a methyl ester using methanol and mild conditions.

Step H may be carried out in a conventional manner for forming an amide from a methyl ester using ammonia and mild conditions.

Step I is a reduction suitably carved out with, eg. lithium aluminum hydride, at 30° C. to 85° C.

The cyclization reaction of Step J and the conversion to the methylthio derivative in Step K may be carried out as described in U.S. Pat. No. 3,868,372, to obtain the compound IIIA in S-) form.

By selecting and working with the compound VIII in R-) form from Step F, Steps G to K may be carried out to obtain the compound IIIA in R-) form.

For preparing the individual isomers of the formula IIIA in which n is 2 one may begin with the known compound of the formula XIII and proceed according to the following reaction scheme:

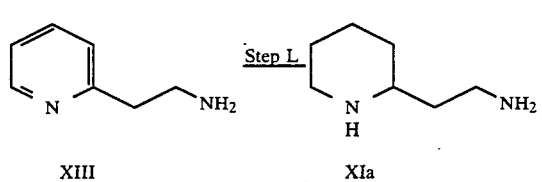

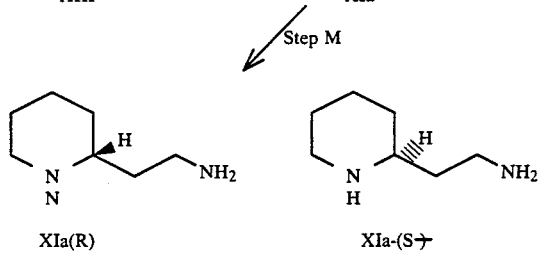

and then proceed with Steps J and K as previously described. Steps L and M may be carried out analogously to Steps E and F, respectively.

The individual optical isomers of the compounds I in which n is 1 and p is 0 may be prepared starting with the known natural compound L-proline. The following scheme for producing the S-isomer from L-proline (compound XIV) may be repeated to obtain the R-isomer by starting with D-proline.

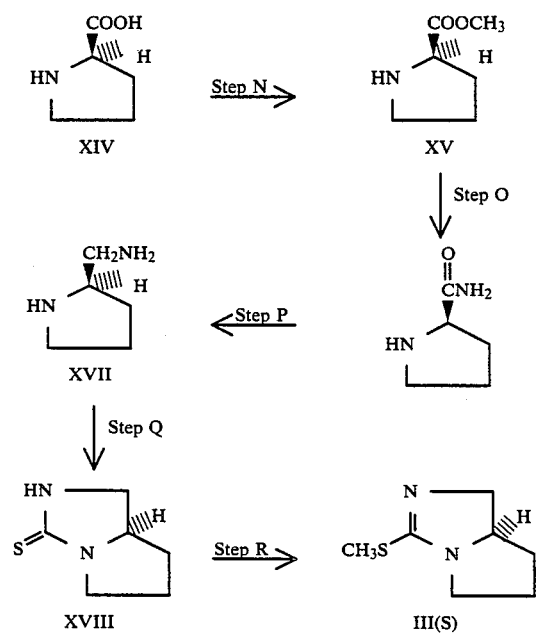

followed by reacting the compound IIID-(S) with a compound of the formula II to obtain the desired compound of the formula I, or by reacting compound III (S) with a compound of th formula VI by Step D to obtain a compound V which is converted by Step C to the desired compound I.

In the above reaction scheme Steps N, O, P, Q and R may be carried out analogously to Steps G, H, I, J and K, respectively, as above described.

The individual opticals isomers of the compounds I in which N is 2 and P is 0 may be also prepared starting with individual optical isomers of proline according to the following reacting scheme for producing the S-isomers.

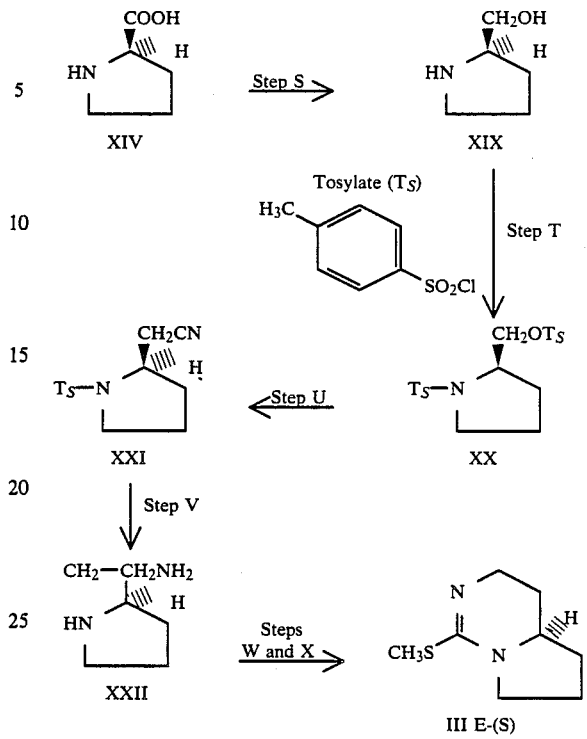

followed by reacting the compound IIIE-(S) with a compound of the formula II to obtain the desired compound of the formula I, or by reacting compound IIIE-(S) with a compound of the formula VI by the reaction of Step D to obtain a compound V which is converted by the reaction of Step C to the desired compound I. As will be evident, the R isomers of the compounds I in which N is 2 and P is 0 may be prepared analogously by starting with the R-proline in the above reaction scheme.

In the above reaction scheme Step S may be suitably effected as a standard reduction reaction employing lithium aluminum hydride in a conventional solvent such as tetrahydrofuran at about room temperatures in an inert atmosphere, e.g. nitrogen.

Step T is a tosylation reaction which may be carried out conventionally employing 4-sulfonylchloride toluene in a pyridine solvent.

Step W is a reaction of known type suitables carried out with potassium cyanide and acetanitrile under reflux conditions.

Step V is a standard cyanide reduction which may be suitably carried out with lithium aluminum hydride in tetrahydrofuran at reflux temperature in an inert atmosphere, e.g. nitrogen.

Also within the scope of the novel compounds provided by the invention are pharmaceutically acceptable salts not materially affecting the pharmacological effect of the compounds of formula I. Such salts include the acid addition salts, e.g., the hydrochloride, fumarate, acetate, citrate, sulfonate, malonate, tartrate, methanesulfonate and hydrosulfate. The acid addition salts may be produced as desired from the corresponding free bases by conventional procedures. Conversely, the free bases may be obtained from the salts by procedures known in the art.

The compounds of the formula I exhibit a Central Nervous System depressant effect in mammals and are useful as minor tranquilizers, particularly for lessening anxiety and/or tension, as indicated by: (1) the ability to reduce conflicts in the Geller Conflict test in rats (1-20 mg/kg.) by the method basically described by I. Geller, Psychopharmacologia, Vol. 1, pages 42-492 (1960) and in modifications thereof as described by Gardner and Piper, Eur. J. Pharmacol. 83, 25 (1982); and (2) the Flunitrazepam Receptor Binding Assay in accordance with the method basically described by R. C. Speth et al., *Life Science*, 22: 859 (1978). Routine and non-substantive modifications of the Flunitrazepam Receptor Binding Assay that are evident from the following description are employed in such evaluation in which non-radioactive candidate compounds are tested for their ability to displace $^3$H-flunitrazepam binding from isolated calf brain benzodiazepine receptors. Hence, an aliquot of frozen calf caudate tissues is thawed and diluted with 0.5M Tris buffer containing metal ions (120 mM NaCl, 5 mM KCL, 2 mM $CaCl_2$ and 1 mM $MgCl_2$) to a final concentration of 8 mg/ml, i.e., a 25 fold dilution. This suspension is made homogenous by homogenation with a Brinkmann Polytron using a rheostate setting of 8 for 10 seconds. Ten $\lambda$ of $^3$H-flunitrazepam solution is diluted in 0.05M Tris buffer (pH 7.1 at 37° C.) to give a concentration of 10 nM ($3.13 \times 10^{-6}$ mg/ml). This solution is stored frozen at $-20°$ C., while the stock $^3$H-flunitrazepam solution in ethanol is kept refrigerated at $+2°$ C. Periodically, the stock ethanolic $^3$H-flunitrazepam solution is examined by TLC for chemical purity. If the purity becomes <90%, the stock solution is repurified or new high purity $^3$H-flunitrazepam is obtained and the impure $^3$H-flunitrazepam discarded. A 0.1 ml portion of 10 nM $^3$H-flunitrazepam "working" solution is added to $12 \times 75$ mm borosilicate disposable test tube along with 0.1 ml of freshly prepared 10% ethanol solution. This is the control tube for measuring total binding. Non-specific binding is determined by the addition of $2 \times 10^{-5}$ diazepam (in 10% ethanol) to other tubes in the place of 0.1 ml 10% ethanol. The specific binding is determined in the final results by subtraction of the non-specific binding from the total binding. All compounds screened have their results expressed in terms of specific binding and are tested at a final concentration of $1 \times 10^{-6}$M. For simplicity and expediance, it is assumed that all compounds have an average molecular weight of 300 a.m.u. and that 3 compounds are screened simultaneously, since control studies have demonstrated that there is no interaction between compounds. Three mg of each compound are placed in $18 \times 150$ mm borosilicate disposable test tubes. These tubes are kept in the dark at room temperature until the day of the assay at which time 10 ml of absolute ethanol is added and the tubes placed in a Branson Ultrasonic Cleaner for 15 minutes and then vortexed in order to put the compounds into solution. All tubes are closely examined to make certain the compounds are completely in solution. If not, 3 drops of 2N HCl is added. If the compound(s) are still not in solution but a cloudy homogenous suspension is found, then the subsequent dilutions are continued. If large insoluble particles are found, then each compound is tested separately at a later time. This gives a concentration of $\sim 1 \times 10^{-3}$M. The compounds are further diluted by serial dilution as follows: 0.1 ml of the $10^{-3}$M solution is added to 0.9 ml of 100% ethanol and vortexed. A 0.1 ml portion of this solution is added to 0.9 ml of water to give $\sim 1 \times 10^{-5}$M solution. A 0.1 ml portion of this solution is added to $12 \times 75$ mm test tubes for assay. All assays are run in duplicate. A 0.8 ml portion of caudate tissue suspension is added to all tubes, vortexed, incubated at 2° C. for 120 minutes, and rapidly filtered under vacuum through Whatman GF/G glass fiber filters. Each tube is rinsed once with 3 ml ice-cold 50 mM Tris buffer (pH 7.1 at 37° C.) and the filter subsequently washed once with 6 ml of the same Tris buffer. The $^3$H-flunitrazepam trapped on the filters is counted by liquid scintillation counting on a Beckman LS 8000 after the filters are rapidly shaken for 45 minutes in the scintillation vials with 10 ml of scintillation cocktail. Results of compounds screened are calculated by the on-line data reduction system in the Beckman LS 8000, and are expressed as a percent specifically bound compared to control.

Benzodiazepine receptors are obtained from male Holstein calves. Immediately after exsanguination, the brains are quickly removed and placed in ice. Dissection of the caudate nucleus is completed within 2 hours after sacrifice and the tissue weighed, and homogenized (1:10, W/V) in 0.05M Tris buffer (pH 7.1 at 37° C.) using a Brinkmann Polytron for 10 seconds with a rheostat setting of 8. The homogenate is centrifuged for 10 minutes at 20,000 RPM in a Sorvall RC2B centrifuge using a SS 34 head. The supernatant is decanted and the pellet washed twice to remove endogenous dopamine by resuspension with the use of the Brinkmann Polytron and recentrifugation. The final pellet is resuspended in 0.05M Tris (pH 7.1 at 37° C.) containing 120 mM NaCl, 5 mM KCl, 2 mM $CaCl_2$, and 1 mM $MgCl_2$ in a final concentration of 200 mg wet weight starting material/ml of buffer. The homogenate is stored in 4 ml aliquots in glass bottles in liquid nitrogen.

Substantially similar results are obtainable in a Flunitrazepam Receptor Binding Assay (FBA) as described by Chang et. al., Eur. J. Pharmacol., 48, 213 (1978): when carried out with the non-substantive modifications evident from the following description (hereinafter FBA TEST No. (2): Fresh calf brain cortex is homogenized in a 19 fold volume of Tris-HCl buffer pH 7.4, using a Brinkman Polytron PT 20 and centrifuged at 50'000 g for 10 min. The pellets are frozen at $-20°$ C. and resuspended in a 400 fold volume of Tris-buffer pH 7.4 before use for the binding assay. The assay mixtures consist of 1.8 ml of homogenate (corresponding to 4.5 mg of original tissue), 0.1 ml [$^3$H]-Flunitrazepam (final concentration 1.5 nM), and 0.1 ml of buffer for determination of total binding or 0.1 ml of unlabelled Flunitrazepam (final concentration 1 $\mu$M) for determination of nonspecific binding, respectively. To assess the potency of various drugs in inhibiting specific binding, drugs are added (instead of buffer) to give 5 to 9 different concentrations between 1 nM and 10 $\mu$M, each in duplicate. After incubation for 15 min at 0° C., the assay mixtures are rapidly filtered through Whatman GF/B filters and washed twice with 5 ml of ice cold Tris-buffer. The filters are counted in Rialuma on a LKB Rach-Beta Liquid Scintillation Counter. $IC_{50}$ values (concentration of a test drug which inhibits specific binding of $^3$H-Flunitrazepam by 50%) are determined by linear regression analysis (HILL-Plot).

The compounds of formula I possess a relatively high level of activity in the above-indicated tests and possess an interesting and desirable spectrum of tranquilizer activity, particularly anti-anxiety activity. The compounds of formula I are also indicated to have a stimulating effect on behavior as measured in observation tests and to lack undesirable CNS depressant effects such as ataxia. For example, the compounds of the formula I are indicated to have some activity in the hexobarbital reinduction test. However, at the doses at which the compounds are indicated to be useful as minor tranquilizers, e.g. by the FBA test and the conflict segment of the Geller Conflict test, the racemates of the compounds I, e.g. the compound of Example 1 hereinafter, are generally indicated to be only mildly active or essentially inactive in a number of other standard CNS depressant tests, such as in sleep studies in monkeys and rats, spinal reflex test in cats, the chemically induced convulsions test (in mice with N-sulfamoylhexahydrolazepine), the Dunham rotarod test and, of further interest, in the variable interval segment of the Geller Conflict test. The compounds I in racemate form are therefore indicated to have a very specific and desirable mode of action in effecting tranquilization, and in particular are indicated to effect tranquilization with a substantially reduced sedative action which is associated with, e.g. drowsiness, in most if not all of the currently available tranquilizers. In particular, the compounds are indicated to be superior to the conventional benzodiazepine tranquilizers, e.g. diazepam, by having a considerably lesser sedative component as determined in the above-indicated sleep studies. Also, the compounds I do not interact with and potentiate the effects of alcohol.

Surprisingly interesting and useful results were found upon separation of the racemates of the compounds of the formula I into their individual optical isomers (antipodes). While the racemates and individual optical isomers were indicated to have about the same level of activity in FBA tests specifically indicating tranquilizing activity, a marked difference was found between R- and S optical isomers in vivo in tests indicative of sedation. More particularly, in evaluations in which the already reduced sedation effects of the racemate were detected, the sedation effects of the R isomer were only revealed at dosages significantly above those at which tranquilizing activity is indicated. On the other hand, in the case of the S-isomer, the doses producing sedation effects were indicated to substantially overlap those at which tranquilizing activity was indicated. For example, in vivo tests in rats. The S-isomer of Example 9 hereinafter was indicated to have tranquilizing (anxiolytic) action in the dose range of about 2 to 15 milligrams per kilograms and mild sedation-related effects in the dose range of about 3–50 milligrams per kilogram. On the other hand, the R-isomer of Example 6 showed tranquilizing (anxiolytic) action in the dose range of about 4–40 milligrams per kilogram and weak-to-mild sedation-related effects in the dose range of from 60–120 milligrams and higher. In evaluation of the optical isomers in rats to obtain the above indications, the Discrimination Test and the conflict segment (number of lickings) of Geller Conflict Test were used to evaluate tranquilizing activity. In the Discrimination Test, the R-isomer had an $ED_{50}$ of 4.2 mg/kg. and the S-isomer an $ED_{50}$ of 2.6 mg/kg. In the conflict test, the R-isomer was indicated to have a minimum effective dosage of 30 mg/kg. and the S-isomer a minimum effective dosage of 10 mg/kg. In tests indicative of sedation, the R-isomer was indicated in the Rotarod, Locomotion and Rearing Tests to have an $ED_{50}$ greater than 120 mg/kg. and a minimum effective dose of 60 mg/kg. in sleep studies (sleep/wakefulness studies). On the other hand, the S-isomer was indicated to have an $ED_{50}$ between 40–50 mg/kg. in the Rotarod, Locomotion and Rearing Tests and a low minimum effective dose of 3 mg/kg. in the Sleep Studies.

Since the overall sedative effects of the S-isomers are milder than in the case of Diazepam, such isomers may be employed as tranquilizers but will be more suitably employed where sedative effects are desired, such as at bedtime.

On the other hand, the R-isomers with their substantial freedom from sedative effects represent highly desired tranquilizers useful in many situations where conventional tranquilizers with their sedative side effects have been a problem or cause for concern. The overall spectrum of the R-isomers as tranquilizers is particularly desirable for use in areas such as geriatric medicine where the sedative effects of other tranquilizers can have exaggerated undesired effects.

For such use as minor tranquilizers, particularly in the relief of anxiety and/or tension, the amount of the compounds of the formula I to be administered will vary depending upon the compound used, mode of administration, severity of the condition being treated and other known factors. However, in general, satisfactory results are obtained when administered at a daily dosage of from 0.1 to 60 milligrams per kilogram of body weight, preferably given orally and in divided doses 2 to 4 times a day, or in sustained release form. For larger mammals the administration of from 10 to 500 milligrams per day provides satisfactory results and dosage forms for internal administration comprise from 2.5 to 250 milligrams of the compound in admixture with a solid or liquid carrier. The daily dosage for larger mammals is preferably from 10 to 200 milligrams and dosage forms preferably contain from 2.5 to 100 milligrams.

Pharmaceutical compositions provided by the invention and useful for effecting tranquilization of mammals contain a compound of the formula I as active ingredient and one or more conventional pharmaceutically acceptable carriers, including such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like. e.g., a sterile injectable aqueous suspension. Such compositions, including applicable unit dosage forms thereof, may be prepared according to any method known in the art for the manufacture of pharmaceutical compositions. The compositions of the invention adapted for oral or parenteral administration may contain from 1% to 90% by total weight of active ingredient in combination with the carrier, more usually 3% to 60%. The preferred unit dosage forms are the essentially solid forms adapted for oral administration.

A representative formulation for administering 3 to 4 times a day or as needed in treatment of anxiety and/or tension is a capsule prepared by conventional capsulating techniques and containing the following ingredients:

| Ingredient | Parts by Weight |
|---|---|
| (−)-10aR-7,8,9,10,10a,11-hexahydro-2-trifluoromethyl-13H-pyrido[1′,2′:3,4]imidazo[2,1-b]quinazolin-13-one | 10 |

11

-continued

| Ingredient | Parts by Weight |
|---|---|
| Lactose | 200 |

It will be evident that the compounds of the formula I may exist in the form of both geometric and optically active isomers and the individual isomers may be separated and recovered by conventional techniques when found together in the reaction product. Analysis of the reaction product of Example 1, hereinafter, indicates the same to be a racemic mixture substantially only the trans isomer which geometric form is also indicated to be generally preferred for all compounds of the formula I based on ease of preparation and high biological activity.

The following examples are for purposes of illustration only.

EXAMPLE 1

Trans(e,e)-( )-2-trifluoromethyl-7,8,9,10,10a,11-Hexahydro-13H-pyrido[1',2':3,4]-imidazo[2,1-b]-quinazolin-13-one

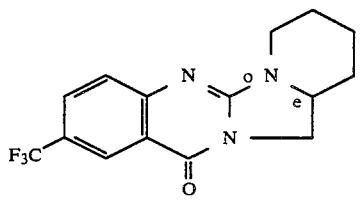

To a solution of 10 grams of 1,5,6,7,8,8a-hexahydro-3-methylthio-imidazo[1,5-a]pyridine in 60 ml. of dry dimethylacetamide is added 12 grams of 2-amino-5-trifluoromethylbenzoic acid. The resulting solution is stirred at reflux for 18 hours. The resulting reaction solution is then evaporated to dryness, the residue dissolved in methylene chloride, washed with 2N sodium hydroxide solution, filtered, dried with anhydrous magnesium sulfate and concentrated in vacuo. The residue is crystallized from ethanol/diethyl ether (1:1.25) to obtain the title compound, m.p. 152°–154° C., which produces an $ED_{50}$ of 15 mg/kg. P.O. in evaluation according to the above referred to Geller Conflict test. In the FBA test (Chang et al. modification) the compound produces an $IC_{50}$ of 6.5 nM.

EXAMPLE 2

Following the procedure of Example 1 on substitution of the appropriate starting materials, and after crystallization there is also obtained the following compound conforming to the structural formula I:

(a) 2-trifluoromethyl-7,8,9,10,10a,11,12,13-octahydro-14H-pyrido[1',2':3,4]pyrimido[2,1-b]quinazolin-14-one.

EXAMPLE 3

(+)-8aR-1,5,6,7,8,8a-Hexahydro-3-methylthio-imidazo[1,5-a]pyridine

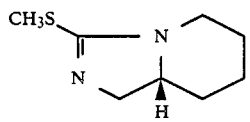

Step A: Resolution of (+)-α-pipecolic acid (piperidine-2-carboxylic acid)

387 g of racemic pipecolic acid are suspended in 1.5 liters of hot methanol and 450 g of L-(+)-tartaric acid thoroughly stirred in. Shortly after a clear, dark solution is obtained which is seeded and allowed to crystallize. The crystals are filtered off and washed well with $CH_3OH$. The light-gray crystals are dried to obtain 370 g of product, m.p. 189°–190°, which is dissolved in 350 ml of water and 175 ml of hot acetone, resulting dark solution filtered with active charcoal and the then almost colorless solution diluted with 800–900 ml of acetone until cloudiness sets in. The resulting crystals are filtered off and thoroughly washed with acetone/water ca. 4:1. A second fraction may be obtained by strong concentration (incl. $H_2O$) and repeated dilution with acetone to obtain the (+)-tartrate of pipecolic acid, $[\alpha]_D^{20} = +21°$ (C=2, $H_2O$), weight=316 g m.p.=195°–196°.

About 3 liters of Amberlite 7R-120 in $H^+$ form are prepared and 720 g of (+)-tartrate of pipecolic acid dissolved in 1 liter $H_2O$ passed through the Amberlite column. After washing out the tartaric acid with 10% ammonia the (+)-pipecolic acid is eluted. M.P. 277°–279° (decomp) $[\alpha]_D^{20} = +25°$ (C=1.5, $H_2O$). Single recrystallization from $H_2O$/alcohol (ca 1:3 to 1:5) yielded a total of 290 g (+)-pipecolic acid ((+)-2R-piperidine-2-carboxylic acid).

Step B: (+)-2R-Piperidine-2-carboxylic acid methyl ester

HCl gas is passed through 2 liters of absolute methanol until a molarity of 6.5 is achieved. 265 g of D-(+)-pipecolic acid are scattered in and the clear solution which results after about 1 hr. is allowed to stand overnight at R.T. The resulting mixture is strongly concentrated at a maximum bath temperature of 38°, poured onto ice, neutralized to pH 9–10 with $K_2CO_3$ and extracted four times with dichloromethane to obtain the above product, b.p. 72°–75°/9 mm.

Step C: (+)-2R-Piperidine-2-carboxylic acid amide 19 g of the product of Step B is dissolved in 20 ml concentrated ammonia at RT and allowed to stand overnight. A white crystalline slurry is obtained which contains no further starting material. This is rinsed into a separating funnel with water and extracted 3 times with dichloromethane and then 3 times with dichloromethane plus ca. 20% EtOH. A total of 14 g of white crystals of the above product are obtained after recrystallization from alcohol/hexane, $[\alpha]_D^{20} + 33°$ (C=2, ethanol).

Step D: (−)-2R-2-Aminomethyl-piperidine

The $LiAlH_4$ is slurried in 200 ml of THF and 12.6 g of the product of Step C dissolved in 500 ml THF at 65° is then rapidly poured in while still warm. After 5 hrs refluxing with stirring there is produced a white milky product which is cooled to −15° and treated with 150 ml H₂O and 100 ml THF. After 2 hours without cooling the white suspension is filtered and twice extracted with THF. The filtrates are combined and concentrated. The resulting oil which contains considerable H₂O is taken up in methylene chloride, separated from the water, twice re-extracted, dried and concentrated. The resulting oil is distilled to obtain the above product, $[\alpha]_D^{20} -19.1$ (C=2, ethanol).

Step E: (+)-8aR-1,5,6,7,8,8a-Hexahydroimidazo[1,5-a]pyrimidin-3(2H)thione

The product of Step D is reacted with carbon disulfide in pyridine for 6 hours at 100° C. to obtain the above product, $[\alpha]_D^{20} +39.5$ (C=2, ethanol).

Step F: (+)-8aR-1,5,6,7,8,8a-Hexahydro-3-methylthio-imidazo[1,5-a]pyridine

The product of Step E is reacted with methyliodide in methanol in the presence of sodium hydroxide to obtain the above product, $[\alpha]_D^{20} +57.5$ (C=2, ethanol).

EXAMPLE 4

(+)-10aR-2-iodo-7,8,9,10,10a,11-hexahydro-13H-pyrido[1,′2′:3,4]imidazo[2,1-b]quinazolin-13-one

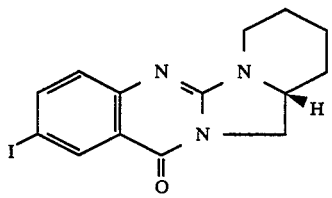

A mixture of 6.8 g (40 mM) of (+)-8aR-1,5,6,7,8,8a-hexahydro-3-methylthio-imidazo[1,5-a]pyridine and 10.6 g (40 mM) of 2-amino-5-iodobenzoic acid in 30 ml of dimethylacetamide is heated under an argon atmosphere for 4 hours at 145° C. The solvent is evaporated under high vacuum and the residue taken up in 1n caustic soda/methylene chloride. The crude product is crystallized from methanol and recrystallized from methanol/methylene chloride to obtain the above product, m.p. 174°–175° C., $[\alpha]_D^{20} +7.4°$ (C=2, pyridine) and $[\alpha]_D^{20} +3.7°$ (C=2.5, methylene chloride).

EXAMPLE 5

(−)-10aR-7,8,9,10,10a,11-hexahydro-2-trifluoromethyl-13H-pyrido[1,′2′:3,4]imidazo[2,1b]quinazolin-13-one

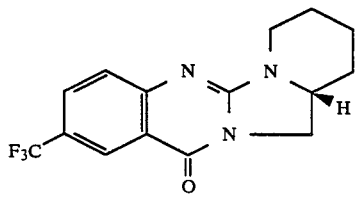

A solution of 3.67 g of (+)-10aR-2-iodo-7,8,9,10,10a,11-hexahydro-13H-pyrido[1,′2′:3,-4]imadazo[2,1-b]quinazolin-13-one in 8 ml. of N-methylpyrrolidone is treated with 5.44 g of trifluoroacetic acid and 3.85 g of copper iodide and heated for 2 hours under an argon atmosphere at 150° C. The resulting dark solution is concentrated under high vacuum, taken up in 1N sodium carbonate and methylene chloride, extracted, dried and concentrated by evaporation and then chromatographed over silica gel (250 g). The product is crystallized from methylene chloride and recrystallized from methanol/water (1:1) to obtain the above product, m.p. 156°–157° C., $[\alpha]_D^{20} -2.8°$ (C=3, pyridine), $[\alpha]_D^{20} -2.20$ (C=2.5, methylene chloride).

EXAMPLE 6

(−)-8aS-1,5,6,7,8,8a-hexahydro-3-methylthio-oimidazo[1,5-a]pyridine

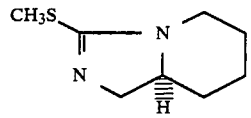

Step A: Recovery of (−)-S-Pipecolic acid 483 g (=3.75M) of enriched (−)-pipecolic acid are suspended in 3 liters of hot methanol. 565 g of D-(−)-tartaric acid are rapidly scattered in and an attempt made as quickly as possible to obtain a solution. Crystallization commences before a complete dissolution can be achieved. The mixture is cooled, filtered and well washed with methanol. The filtrate is concentrated and recrystallized. The obtained crystals are dissolved hot in ca 800 ml of water and 400 ml at acetone and treated with active charcoal. The clear almost colorless filtrate is diluted with ca 2 liters of acetone. The resulting crystals are filtered of and well washed with acetone/H₂O 4:1 followed by 100% acetone. The filtrate is concentrated and diluted with acetone to obtain a second fraction. Both fractions are dried. $[\alpha]_D^{20} =20.3°$ for the first fraction and −20.7° for the second fraction, (c=2, H₂O) total weight 706 g. Separation is effected with 3 liters of Amberlite 7R 120 in the H⁺ form. After working the tartrate salt with 10% ammonia, the L-(−)-pipecolic acid is obtained by elution and concentration by evaporation and then once recrystalized out of a minimum of H₂O and a maximum of alcohol, $[\alpha]_D^{20} -27.5$ (C=2, H₂O).

Steps B and C: (−)-2S-Piperidin-2-carboxylic acid amide

Following the procedure of Steps B and C of Example 4, above, there is obtained the above compound, $[\alpha]_D^{20} -33°$ (C=2, ethanol).

Step D: (+)-2R-2-Aminomethyl-piperidine 100 g of amide obtained above are added in portions under argon at 20°–30° C. to 60 g of LiAlH₄ in 2.5 liters of dry THF. The temperature of the suspension is raised to 65° C., refluxed for 5 hours and allowed to stand at RT overnight. The resulting mixture is treated at −20° C. with 600 ml of H₂O-THF (1:1), filtered, well washed and concentrated. The resulting oil is distilled under H₂O-vacuum to obtain the above compound, $[\alpha]_D^{20} +18°$ (C=2, ethanol), b.p. 62°–64° at 11 mm.

Step E: (−)-8aS-1,5,6,7,8,8a-Hexahydroimidazo[1,5-a]pyrimidin-3(2H)thione

The product of Step D is reacted with carbon disulfide in pyridine for 6 hours at 100° C. to obtain the above product, $[\alpha]_D^{20} -39.5$ (C=2, ethanol).

Step F: (−)-8aS-1,5,6,7,8,8a-Hexahydro-3-methylthio-oimidazo[1,5-a]pyridine

The product of Step E is reacted with methyliodide in methanol in the presence of sodium hydroxide to obtain the above product, $[\alpha]_D^{20} -60°$ (C=2, ethanol).

EXAMPLE 7

(−)10aS-2-iodo-7,8,9,10,10a,11-hexahydro-13H-pyrido[1,'2':3,4]imidazo[2,1-b]quinazolin-13-one

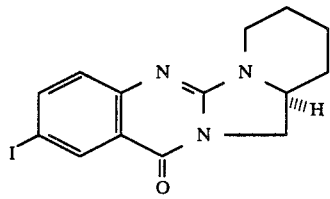

A mixture of 6.8 g (40 mM) of (−)-8aS-1,5,6,7,8,8a-hexahydro-3-methylthio-imidazo[1,5-a]pyridine and 10.6 g (40 mM) of 2-amino-5-iodobenzoic acid in 30 ml of dimethylacetamide is heated under an argon atmosphere for 4 hours at 145° C. The solvent is evaporated under high vacuum and the residue taken up in 1N caustic soda/methylene chloride. The crude product is crystallized from methanol and recrystallized from methanol/methylene chloride to obtain the above product, m.p. 174°–175° C., $[\alpha]_D^{20}$ −7.5 (C=3, pyridine) and $[\alpha]_D^{20}$ −3.7° (C=3, methylene chloride).

EXAMPLE 8

(+)-10aS-7,8,9,10,10a,11-Hexahydro-2-trifluoromethyl-13H-pyrido[1,'2':3,4]imidazo[2,1b]quinazolin-13-one

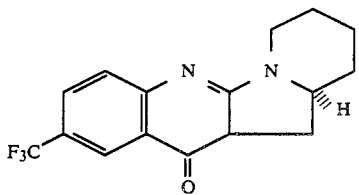

A solution of 3.67 g of (+)-10aR-2-iodo-7,8,9,10,10a,11-hexahydro-13H-pyrido[1',2':3,-4]imadazo[2,1-b]quinazolin-13-one in 8 ml. of N-methylpyrrolidone is treated with 5.44 g of trifluoroacetic acid and 3.85 g of copper iodide and heated for 2 hours under an argon atmosphere at 150° C. The resulting dark solution is concentrated under high vacuum, taken up in 1N sodium carbonate and methylene chloride, extracted, dried and concentrated by evaporation and then chromatographed over silica gel (250 g). The product is crystallized from methylene chloride and recrystallized from methanol/water (1:1) to obtain the above product, m.p. 156°–157° C., $[\alpha]_D^{20}$ +3.15° C=3, pyridine), $[\alpha]_D^{20}$ +2.15° (C=2.5, methylene chloride).

What is claimed is:

1. The compound which is trans(−)-10aR-7,8,9,10,10a,11-hexahydro-2-trifluoromethyl-13H-pyrido[1',2':3,4]imidazo[2,1b]quinazolin-13-one or a pharmaceutically acceptable acid addition salt thereof, said compound being substantially free of its corresponding S-optional isomer form.

2. A pharmaceutical composition comprising an inert pharmaceutically acceptable carrier and a tranquilizing effective amount of the compound of claim 1.

3. A pharmaceutical composition according to claim 2 which contains 2.5–250 milligrams of the compound.

4. A method of tranquilizing a mammal comprising administering to a mammal a tranquilizing effective amount of the compound of claim 1.

5. A method according to claim 4 in which 10–200 milligrams per day of the compound is administered.

* * * * *